United States Patent [19]
Carley et al.

[11] Patent Number: 5,859,063
[45] Date of Patent: Jan. 12, 1999

[54] USE OF CERTAIN N-ACETONYLBENZAMIDES AS FUNGICIDES

[75] Inventors: H. Edwin Carley, Chalfont; Ashok K. Sharma, Horham, both of Pa.

[73] Assignee: Rohm and Haas Company, Philadelphia, Pa.

[21] Appl. No.: 333,362

[22] Filed: Apr. 4, 1989

Related U.S. Application Data

[62] Division of Ser. No. 634,916, Jul. 26, 1984, Pat. No. 4,822,902.

[51] Int. Cl.$^6$ .................................................. A01N 37/18
[52] U.S. Cl. .......................... 514/617; 514/521; 558/392; 564/186
[58] Field of Search ........................... 564/186; 514/617, 514/521; 558/392

[56] References Cited

U.S. PATENT DOCUMENTS

| | | | |
|---|---|---|---|
| 3,661,991 | 5/1972 | McNulty et al. | 564/186 |
| 4,425,357 | 1/1984 | Bosone et al. | 514/617 |
| 4,470,973 | 9/1984 | Natarajan et al. | 548/180 |
| 4,647,582 | 3/1987 | Takahashi et al. | 514/521 |
| 4,710,514 | 12/1987 | Takahashi et al. | 558/392 |
| 4,822,902 | 4/1989 | Carley et al. | 558/392 |

*Primary Examiner*—Brian M. Burn
*Attorney, Agent, or Firm*—Thomas D. Rogerson

[57] ABSTRACT

Certain N-acetonylbenzamides exhibit low toxicity to plants are particularly useful for control of fungi, especially Phycomycetes.

19 Claims, No Drawings

USE OF CERTAIN N-ACETONYLBENZAMIDES AS FUNGICIDES

This is a division of application Ser. No. 634,916, filed Jul. 26, 1984, now U.S. Pat. No. 4,822,902.

BACKGROUND OF THE INVENTION

This invention relates to a method of controlling phytopathogenic fungi by the use of a fungicidally effective amount of certain N-acetonylbenzamides which exhibit low phytotoxicity to the plant as well as the use of such compounds in fungicidal compositions.

It is known that the benzamides in the class of N-(1,1-dialkyl-3-chloroacetonyl) substituted benzamides have fungicidal activity; see, for example, U.S. Pat. No. 3,661,991 and 3,751,239 However, such compounds, wherein the terminal carbon can only be substituted by chloro or hydrogen atoms, are so phytotoxic that they have no practical use in the treatment of fungal plant infections of plants.

The present invention recognizes that the phytotoxicity of such N-chloroacetonylbenzamides can be reduced by altering the substituents on the carbon of the acetonyl group to other than only hydrogen or chlorine.

DESCRIPTION OF THE INVENTION

Foliar or soil-borne phytopathogenic fungi are controlled by applying a fungicidally effective amount of compounds of formula (I):

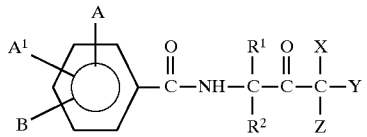

(I)

wherein A is a hydrogen, chloro, bromo, fluoro, iodo, trifluoromethyl, trifluoromethoxy, fluorosulfonyl (—FSO$_2$), methyl, ethyl, phenyl, methoxy, chloromethyl, (C$_1$–C$_2$)-alkoxycarbonyl, cyano or hydroxy group;

A$^1$ and B are each independently selected from hydrogen, chloro, bromo, fluoro and methyl group;

X is bromo, iodo, fluoro, cyano, thiocyano (—SCN), isothiocyano (—NCS), methylsulfonyloxy (—OSO$_2$CH$_3$), thio(C$_1$–C$_2$)alkyl (—SR), (C$_1$–C$_2$) alkoxy (—OR), carbamoyl of the formula (—OC(O)NR$^3$)$_2$), dithiocarbamoyl (—SC(S)NR$^3$), hydroxy (—OH), azide (—N$_3$), (C$_1$–C$_4$)alkylcarbonyloxy (—OC(O)R), phenylcarbonyloxy (—OC(O)R$^4$, wherein R$^4$ is the phenyl group), phenoxy, phenylthio, trifluoromethylcarboxy, imidazolyl or triazolyl group;

Y and Z are each independently a hydrogen, bromo, chloro, iodo, fluoro, cyano, thiocyano (—SCN), isothiocyano (—NCS), methylsulfonyloxy (—OSO$_2$CH$_3$), thio(C$_1$–C$_2$)-alkyl (—SR), (C$_1$–C$_2$) alkoxy (—OR), carbamoyl of the formula (—OC(O)N (R$^3$)$_2$), hydroxy (—OH), azide (—N$_3$) or (C$_1$–C$_2$) alkylcarbonyloxy (OC(O)R) group and either Y or Z may be an imidazolyl or triazolyl group;

each R is independently an alkyl group;

R$^1$ and R$^2$ are each independently a hydrogen atom or an (C$_1$–C$_6$)alkyl group; and R$^3$ is a hydrogen or a (C$_1$–C$_4$)alkyl group, preferably a hydrogen or a (C$_1$–C$_2$)alkyl group.

When X contains a phenylcarbonyloxy, a phenoxy or phenylthio substituent, the phenyl moiety may be substituted with one substituent selected from the group consisting of chloro, fluoro, bromo, iodo or methyl group.

Preferred methods of the invention utilize compounds of formula (I) wherein A and A$^1$ substituents are at the 3-, 4- or 5-position of the phenyl ring; the A substituent is a chloro, bromo, trifluoromethyl, fluoro or methyl group; the A$^1$ and B substituents are each independently hydrogen, chloro, bromo or fluoro group; R$^1$ and R$^2$ are each independently a (C$_1$–C$_4$)alkyl group; X is bromo, iodo, methylsulfonyloxy, a thio(C$_1$–C$_2$)alkyl, isothiocyano (—NCS) or thiocyano (—SCN) group. Y is a hydrogen, bromo, chloro, cyano or iodo group; and Z is a hydrogen, chloro or bromo group.

More preferred methods of the invention utilize compounds of formula (I) wherein the A, A$^1$ and B substitutes are at the 3-, 4- and 5-position of the phenyl ring; the A substituent is a chloro, bromo, fluoro, trifluoromethyl or methyl group; A$^1$ is a hydrogen, chloro, bromo or fluoro group; B is a hydrogen atom; R$^1$ and R$^2$ are each independently (C$_1$–C$_2$)alkyl; X is a bromo, iodo, methylsulfonyloxy, an isothiocyano or a thiocyano group; Y is a hydrogen, bromo, chloro or iodo atom; and Z is a hydrogen atom. Most preferably, R$^1$ is a methyl group; R$^2$ is an ethyl group; X is a bromo atom; Y is a hydrogen, bromo, iodo or chloro atom; and Z is a hydrogen atom.

Typical compounds representative of those useful in the present invention include:

N-(3'-bromo-1',1'-dimethylacetonyl)-3-chlorobenzamide

N-(3',3'-dibromo-1',1'-dimethylacetonyl)-3-bromobenzamide

N-(3'-iodo-1',1'-dimethylacetonyl)-3-fluorobenzamide

N-(3'-bromo-3'-chloro-1',1'-dimethylacetonyl)-3-chlorobenzamide

N-(1',1'-dimethyl-3'-thiocyanoacetonyl)-3,5-dichlorobenzamide

N-(1',1'-dimethyl-3'-isothiocyanoacetonyl)-3-iodobenzamide

N-(3',3'-dibromo-1',1'-dimethylacetonyl)-3-chloro-5-fluorobenzamide

N-(3',3'-dibromo-1',1'-dimethylacetonyl)-3-chloro-5-bromobenzamide

N-(3',3'-dibromo-1',1'-dimethylacetonyl)-3-chloro-5-iodobenzamide

N-(3',3'-dibromo-1',1'-dimethylacetonyl)-3,5-dibromobenzamide

N-(1',1'-dimethyl-3'-thiomethylacetonyl)-3,5-dibromobenzamide

N-[3'-(1'-bromo-2'-oxopentan)]-3,5-dichlorobenzamide

N-[3'-(1',1'-dibromo-3'-methyl-2'-oxopentan)]-3,5-dichlorobenzamide

N-[3'-(1'-bromo-1'-methylsulfonyloxy-3'-methyl-2'-oxopentan)]-3-chloramethyl-5-chlorobenzamide N-(3'-bromo-3'-azide-1',1'-dimethylacetonyl)-2-cyano-4-chloro benzamide N-(3'-iodo-3'-phenylcarbonyloxy-1',1'-dimethylacetonyl)-3-methoxycarbonylbenzamide N-[3'-(1',1'-dibromo-3'-methyl-2'-oxononan)]-3,5-dichlorobenzamide N-(3'-bromo-3'-chloro-1',1'-dimethylacetonyl)-3,4,5-trichlorobenzamide N-(3'-bromo-3'-chloro-1',1'-dimethylacetonyl)-3,5-dichloro-4-methylbenzamide N-(3'-bromo-3'-chloro-1',1'-dimethylacetonyl)-3-chlorobenzamide N-(3',3'-dichloro-3'-thioethyl-1',1'-dimethylacetonyl)-3-methylbenzamide N-(3',3'-dibromo-3'-cyano-1',1'-dimethylacetonyl)-3-trifluoro-methylbenzamide N-(3',3'-dibromo-1',1'-dimethylacetonyl)-3-methylbenzamide N-(3',3'-dibromo-1',1'-dimethylacetonyl)-3,4-dichlorobenzamide
N-[3'-(1'-bromo-1'-chloro-2'-oxopentan)]-3-chlorobenzamide
N-[3'-(1'-bromo-1'-chloro-2'-oxopentan)]-3,4-dichlorobenzamide
N-[3'-(1'-bromo-1'-chloro-2'-oxopentan)]-3,5-dimethylbenzamide
N-[3'-(1'-bromo-1'-chloro-2'-oxopentan)]-3-chloro-5-methylbenzamide
N-(3',3'-dibromo-1',1'-dimethylacetonyl)-3-cyanobenzamide
N-(3',3'-dibromo-1',1'-dimethylacetonyl)-3-fluorosulphonylbenzamide
N-(3',3'-dibromo-1',1'-dimethylacetonyl)-3-bromomethylbenzamide
N-(3',3'-dibromo-1',1'-dimethylacetonyl)-3-iodobenzamide
N-(3',3'-dibromo-1',1'-dimethylacetonyl)-2,3,4,5,6-pentafluorobenzamide
N-(3',3'-dibromo-1',1'-dimethylacetonyl)-3,5-dichloro-4-methoxybenzamide
N-(3'-methylsulfonyloxy-1',1'-dimethylacetonyl)-3,5-dichlorobenzamide
N-(3'-trifluoroacetyl-1',1'-dimethylacetonyl)-3,5-dichlorobenzamide
N-(3'-azido-1',1'-dimethylacetonyl)-3,5-dichlorobenzamide
N-(3',3',3'-tribromo-1',1'-dimethylacetonyl)-3,5-dichlorobenzamide
N-(3',3'-dibromo-3'-chloro-1',1'-dimethylacetonyl)-3,5-dichloro benzamide
N-[3'-(1'-chloro-1'-bromo-3'-methyl-2'-oxopentan)]-3-chloromethyl benzamide Preferred compounds include:

N-[3'-(1'-bromo-1'-fluoro-3'-methyl-2'-oxopentan)]-3-chlorobenzamide
N-[3'-(1'-bromo-1'-chloro-3'-methyl-2'-oxopentan)]-3-bromobenzamide
N-[3'-(1'-bromo-1'-chloro-3'-methyl-2'-oxopentan)]-3-fluorobenzamide
N-[3'-(1'-bromo-1'-chloro-3'-methyl-2'-oxopentan)]-3-iodobenzamide
N-[3'-(1',1'-dibromo-3'-methyl-2'-oxopentan)]-3-chlorobenzamide and
N-[3'-(1'-bromo-1'-fluoro-3'-methyl-2'-oxopentan)]-3,5-dichloro benzamide
N-[3'-(1'-bromo-1'-chloro-3'-methyl-2'-oxopentan)]-3,5-dichloro benzamide
N-[3'-(1'-bromo-1'-fluoro-3'-methyl-2'-oxobutan)]-3-bromo-5-chlorobenzamide
N-[3'-(1',1'-dibromo-3'-methyl-2'-oxopentan)]-3,5-dichlorobenzamide
N-[3'-(1'-bromo-1'-chloro-3'-methyl-2'-oxobutan)]-3-chloro-5-fluorobenzamide are most preferred.

The present invention provides a means for controlling phytopathogenic Phycomycetes and some fungi classified as Deuteromycetes (Fungi Imperfecti), Ascomycetes, and Basidiomycetes. Important genera of the Phycomycetes include Phytophthora, Plasmopora, Peronospora, and Pseudoperonospora which cause diseases such as potato and tomato late blight, and downy mildew in grapes, squash, melons, broccoli and other cole crops. Basidiomycetes, such as Pellicularia and Puccinia spp. are also controlled by the invention. Species of these genera cause diseases such as rice sheath blight (*Pellicularia filamentosa*) and rusts, e.g., *Puccinia granminis* and *Puccinia recondita*. Plant root and stalk rots caused by Fusarium spp. can also be controlled by the present invention.

Late blights, downy mildews, many root rots and damping-off diseases have been difficult to control due to the lack of effective control methods. Some of the more effective chemical control measures have become ineffective due to the development of resistant fungal strains. The present invention recognizes that the compounds of Formula (I) can be used to control these types of fungi, particularly, late blights and downy mildews, without the high degree of phytotoxicity caused by the benzamides disclosed in the prior art of U.S. Pat. No. 3,661,991 and U.S. Pat. No. 3,751,239.

The benzamides used in the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount is usually from about 0.01 kilogram (kg) to about 20 kg, preferably from about 0.1 to about 5 kg and more preferably from about 0.125 to about 0.5 kg of active ingredient per hectare.

As a seed protectant, the amount of toxicant coated on the seed is usually at a dosage rate of about 10 to about 250 grams (gm) and preferably from about 20 to about 60 gm per 50 kilograms of seed. As a soil fungicide the chemical can be incorporated in the soil or applied to the surface usually at a rate of 0.5 to about 20 kg and preferably about 1 to about 5 kg per hectare. As a foliar fungicide, the benzamide is usually applied to growing plants at a rate of about 0.1 to about 5 and preferably from about 0.125 to about 0.5 kg per hectare.

The process of the present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers* and *Detergents, McCutcheon's Emulsifiers and Detergents/Functional Materials* and *McCutcheon's Functional Materials* all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of N-(1',1'-dimethyl-3',3'-dibromoacetonyl)-3,5-dichlorobenzamide, 45 parts of a synthetic precipitated hydrated silicon dioxide sold under the trademark Hi-Sil® and 5 parts of sodium lignosulfonate (Marasperse® N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex® 7.

Dusts are prepared by mixing the benzamides and salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The benzamides used in the invention can be readily prepared using conventional synthesis techniques. For example, compounds of Formula (I) can be prepared from readily available acetylenic amides (II). When X is a chloro, fluoro, bromo or iodo atom, treatment of the acetylenic amide with a halogen or halogen source ($X_2$), e.g., chlorine, bromine and trifluoromethylhypofluorite at a temperature of from about −30° C. to about 100° C. and preferably at a temperature at from about 0° to about 20° C., either neat or in the presence of a solvent such as methylene chloride, ether, hexane or ethyl acetate, gives an intermediate oxazoline (III) which is readily hydrolyzed under neutral or acidic conditions using an acid such as hydrochloric acid, hydrobromic or sulfuric acid, and using a solvent such as water, methanol, ethanol, isopropanol, tetrahydrofuran, dioxan, acetic acid or dimethylsulfoxide at a temperature of about 10° to about 100° C., preferably at about 35° to about 50° C., to obtain the desired structure (IV).

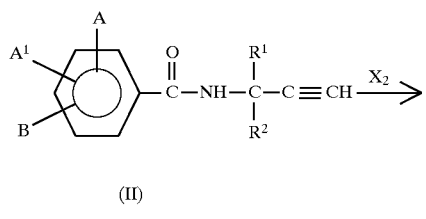

(II)

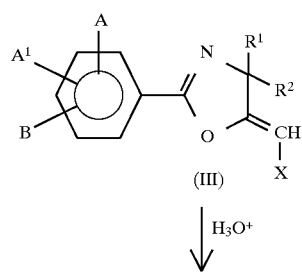

(III)

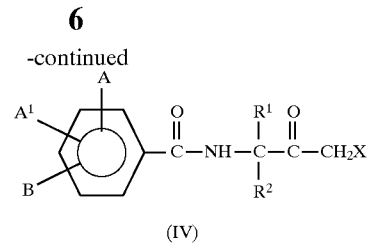

(IV)

When two halogens are desired for X, Y and Z of formula (I), (III) is treated with a second equivalent of the same, i.e., $X_2$, or different halogen, i.e., $Y_2$, under the same general type conditions, as described above to produce the product (V). Hydrolysis of (V) will yield the compounds of structure (VI).

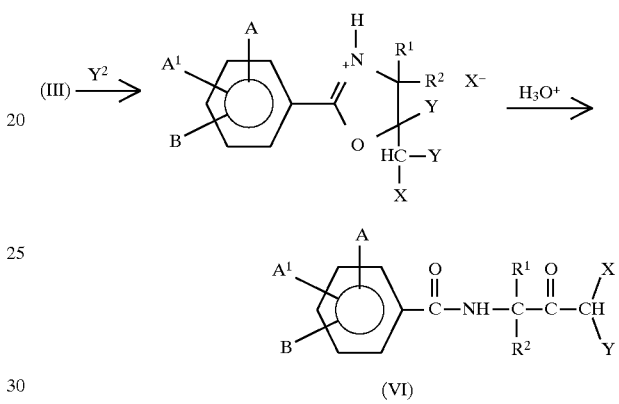

When a substituent other than halogen (X, Y or Z) such as cyano, thiocyano, isothiocyano, ($C_1$–$C_2$)alkoxy, thio ($C_1$–$C_2$)alkyl, dithiocarbamoyl, carbamoyl, azide, trifluoromethylcarboxy, imidazolyl, triazolyl, phenoxy, phenylthio, ($C_1$–$C_2$)alkylcarbonyloxy or phenylcarbonyloxy is desired in a compound of formula (I), it can be readily introduced by the nucleophilic displacement of a chloro or bromo atom of structure (IV) as shown below:

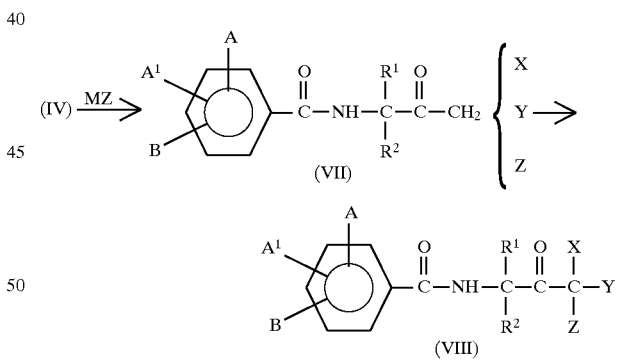

wherein M is an alkali metal cation and X, Y and Z are as defined in formula (I).

Such displacements can also be performed on compounds VI using the salts MZ. Generally this is accomplished by treating compounds of structure IV or VI with an alkali metal (preferably sodium or potassium) salt of X, Y and/or Z in a solvent such as toluene, dimethylformamide (DMF), acetone, dimethylsulfoxide (DMSO), or acetonitrile at a temperature of from about 20° about 100° C.

Additional halogens may be introduced in structure VII by reacting it with one or two equivalents of a halogen ($Cl_2$ or $Br_2$), or a halogenating agent described earlier, to obtain compounds of structure VIII which have two or three non-hydrogen substituents for X, Y and Z.

When X, Y or Z is a hydroxy group, it is prepared by hydrolysis of the corresponding acetate (IX) with potassium carbonate in methanol. (The acetate is prepared by conventional techniques, for example, by reacting compound (IV) with an alkali metal acetate.) The hydroxy ketone (X) may then be converted to its sulfonate ester, e.g., XI, by treatment with a sulfonyl chloride under conventional conditions known in the art.

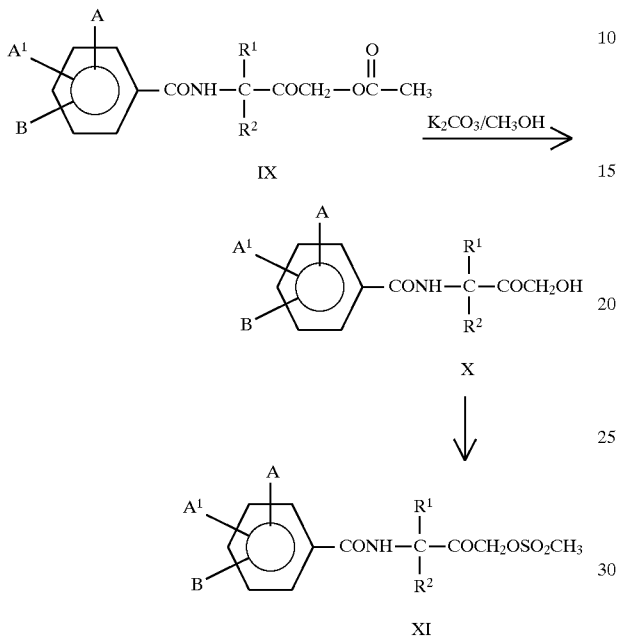

When three halogens are desired in structure I, the oxazoline V is treated with two equivalents of a base like 1,8-diazabicyclo[5.4.0]undec-7-ene (DBU) to obtain XII. This product is treated with another equivalent of halogen and then hydrolyzed to produce structure I which can have three of the same or different halogens.

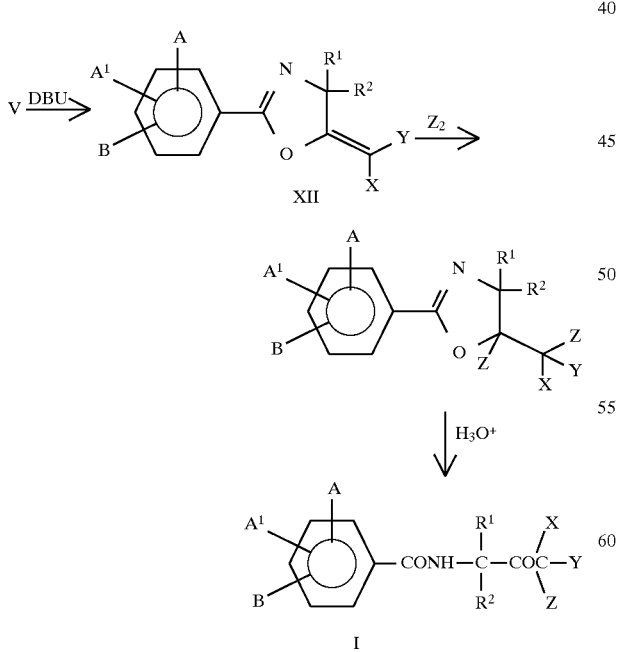

The process of the present invention can also utilize the benzamides in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl -1,3,5-2H-tetrathydrothiadiazine-2-thione (dazomet); and mixtures of these and mixtures with copper salts;

(b) nitrophenol derivatives such as:
dinitro-(1-methylheptyl)phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as:
N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimidophosphorothioate, 4-butyl-1,2,4-triazole, 5-amino-1-[bis-(dimethylamino) phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin); 3-(3,5-dichlorophenyl)-N-(1-methylethyl)-2, 4-dioxo-1-imidazolidinecarboxamide (iprodione); N-(3,5-dichlorophenyl)-1, 2-dimethylcyclopropane-1,2-dicarboximide (procymidone); beta-(4-chlorophenoxy)-alpha-(1,1-dimethylethyl)-1 H-1,2,4-triazole-1-ethanol (triadimenol); 1-(4-chlorophenoxy)-3, 3-dimethyl-1-(1H-1,2,4-triazol1-yl)-2-butanone (triadimefon); beta-[(1,1'-biphenyl)-4-yloxy]-alpha-(1,1-dimethylethyl)-1H -1,2,4-triazole-1-ethanol (bitertanol); 2,3-dichloro-N-(4-fluorophenyl) maleimide (fluoroimide); 1-[2-(2,4-dichlorophenyl)-4-propyl-1,3-dioxolan-2-ylmethyl]-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,4-dichlorophenyl)-5-pyrimidinyl-methanol (triarimol), cis-N-[(1,1,2,2-tetrachloroethyl)thio]-4-cyclohexene-1,2-dicarboximide, 3-[2-(3,5-dimethyl-2-oxycyclohexyl-2-hydroxy]-glutarimide ( cycloheximide), dehydroacetic acid, N-(1,1,2,2-tetrachloroethylthio)-3a,4,7,7a-tetrahydrophthalimide (captafol), 5-butyl-2-ethyl-amino -4-hydroxy-6-methyl-pyrimidine (ethirimol), acetate of 4-cyclodecyl-2,6-dimethyl-morpholine (dodemorph), and 6-methyl-2-oxo-1,3-dithiolo[4,5-b]-quinoxaline (quinomethionate).

(d) miscellaneous halogenated fungicides such as:
tetrachloro-p-benzoquinone (chloranil), 2-3-dichloro-1,4-napthoquinone ( dichlone), 1,4-dichloro-2,5-dimethoxybenzene (chloroneb), 3,5,6-trichloro-o-anisic acid (tricamba), 2,4,5,6-tetrachloroisophthanlonitril (TCPN), 2,6-dichloro-4- nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sulfone, dodecylguanidine acetate (dodine), phenylmercuric acetate, N-ethylmercuri-1,2,3,6,-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano2,4,-dinitrobenzene, 1-phenylthiosemicarbazide, nickel-containing compounds, calcium cyanamide, lime sulfur, 1,2-bis(3,-methoxycarbonyl-2-thioureido) benzene (thiophanate-methyl).

It is particularly advantageous to utilize the present invention in combination with a dithiocarbamate, e.g., mancozeb or maneb, for added control of non-Phycomycetes fungi.

EXAMPLES

The following compounds listed in Tables 1 and 2 are meant to be illustrative of the invention.

TABLE 1

| Example | A | $A^1$ | B | X | Y | Z |
|---|---|---|---|---|---|---|
| 1 | 3-Cl | 5-Cl | H | Br | H | H |
| 2 | 2-Cl | 5-Cl | H | Br | H | H |
| 3 | 3-CH$_3$ | H | H | Br | H | H |
| 4 | 3-OCH$_3$ | H | H | Br | H | H |
| 5 | 3-Cl | 5-Cl | H | Br | Cl | H |
| 6 | 3-Cl | 5-Cl | H | Br | Br | H |
| 7 | H | H | H | Br | Br | H |
| 8 | 3-Cl | H | H | Br | Br | H |
| 9 | 3-Br | H | H | Br | Br | H |
| 10 | 3-CF$_3$ | H | H | Br | Br | H |
| 11 | 3-CH$_3$ | H | H | Br | Br | H |
| 12 | 4-OCH$_3$ | H | H | Br | Br | H |
| 13 | 3-FSO$_2$ | H | H | Br | Br | H |
| 14 | 3-CH$_3$ | H | H | Br | Br | H |
| 15 | 3-I | H | H | Br | Br | H |
| 16 | 3-CH$_3$ | 5-CH$_3$ | H | Br | Br | H |
| 17 | 2-Cl | 4-Cl | H | Br | Br | H |
| 18 | 4-OCH$_3$ | 3-Br | 5-Br | Br | Br | H |
| 19 | 3-Cl | 5-Cl | H | OH | H | H |
| 20 | 3-Cl | 5-Cl | H | —OSO$_2$CH$_3$ | H | H |
| 21 | 3-Cl | 5-Cl | H | OCH$_3$ | H | H |
| 22 | 3-Cl | 5-Cl | H | CN | H | H |
| 23 | 3-Cl | 5-Cl | H | NCS | H | H |
| 24 | 3-Cl | 5-Cl | H | SCN | H | H |
| 25 | 3-Cl | 5-Cl | H | SC(S)NMe$_2$ | H | H |
| 26 | 3-Cl | 5-Cl | H | Br | Br | CN |
| 27 | 3-Cl | 5-Cl | H | CN | Cl | Cl |
| 28 | 3-Cl | 5-Cl | H | SEt | H | H |
| 29 | 3-Cl | 5-Cl | H | SEt | Cl | Cl |
| 30 | 3-Cl | 5-Cl | H | I | I | H |
| 31 | 3-Cl | 5-Cl | H | I | H | H |
| 32 | 3-Cl | 5-Cl | H | Br | CN | H |
| 33 | 3-Cl | 5-Cl | H | Br | Cl | Cl |
| 34 | 3-Cl | 5-Cl | H | Br | Br | Br |

TABLE 1-continued

| Example | A | $A^1$ | B | X | Y | Z |
|---|---|---|---|---|---|---|
| 35 | 3-Cl | 5-Cl | H | Br | Br | Cl |
| 36 | 3-Cl | 5-Cl | H | O-4ClØ* | H | H |
| 37 | 3-Cl | 5-Cl | H | S-4MeØ* | H | H |
| 38 | 3-Cl | 5-Cl | H | SC(S)NMe$_2$ | SC(S)NMe$_2$ | H |
| 39 | 3-Cl | 5-Cl | H | N$_3$ | H | H |
| 40 | 3-Cl | 5-Cl | H | T** | T** | H |
| 41 | 3-Cl | 5-Cl | H | T** | H | H |
| 42 | 3-Cl | 5-Cl | H | T** | Br | H |
| 43 | 3-Cl | 5-Cl | H | I*** | Br | H |
| 44 | 3-Cl | 5-Cl | H | OC(O)CH$_3$ | H | H |

*Ø = phenyl
**T = 1H-1,2,4-triazolyl
***I = 1H-1,3-imidazolyl

TABLE 2

| Example | $A^1$ | $R^1$ | $R^2$ | X | Y | Z |
|---|---|---|---|---|---|---|
| 45 | Cl | H | Et | Br | Br | H |
| 46 | Cl | Me | Et | Br | Br | H |
| 47 | Cl | Me | i-Bu | Br | Br | H |
| 48 | Cl | Me | i-Pr | Br | Br | H |
| 49 | Cl | Et | Et | Br | Br | H |
| 50 | Cl | Me | n-Pr | Br | H | H |
| 51 | Cl | Me | n-Bu | Br | H | H |
| 52 | Cl | Me | n-Pentyl | Br | H | H |
| 53 | Cl | Me | Et | Br | H | H |
| 54 | Cl | Me | Et | SCN | H | H |
| 55 | Cl | Me | Et | Br | Cl | H |
| 56 | H | Me | Et | Br | H | H |
| 57 | H | Me | Et | Br | Br | H |

TABLE 3

| Example | A | $A^1$ | B | $R^1$ | $R^2$ | X | Y | Z |
|---|---|---|---|---|---|---|---|---|
| 58 | Br | H | H | Me | Et | Br | Br | H |
| 59 | Br | H | H | Me | Me | Br | Cl | H |
| 60 | Br | H | H | Me | Et | Br | Cl | H |
| 61 | Br | H | H | Me | Et | Br | H | H |
| 62 | I | H | H | Me | Me | Br | Cl | H |
| 63 | F | H | H | Me | Me | Br | Cl | H |
| 64 | Cl | Cl | H | Me | Et | Cl | Cl | H |
| 65 | Cl | Cl | H | H | n-Pr | Br | H | H |
| 66 | Cl | Cl | H | H | n-Pr | SCN | H | H |
| 67 | Cl | Cl | H | H | n-Bu | Br | H | H |
| 68 | Cl | Cl | H | H | n-Bu | Br | Br | H |

TABLE 3-continued $$\underset{A^1}{\overset{A}{\text{B}}}\text{—}\underset{}{\bigcirc}\text{—CO—NH—}\underset{R^2}{\overset{R^1}{\text{C}}}\text{—CO—}\underset{Z}{\overset{X}{\text{C}}}\text{—Y}$$

| Example | A  | A¹  | B   | R¹ | R² | X                    | Y     | Z |
|---------|----|-----|-----|----|----|----|-------|---|
| 69 | Cl | Cl  | H   | H  | n-Pr | Br                 | Cl    | H |
| 70 | Cl | Cl  | H   | Me | Et | Br                   | F     | H |
| 71 | Cl | Cl  | Cl  | Me | Et | Br                   | Br    | H |
| 72 | F  | Cl  | H   | Me | Me | Br                   | Br    | H |
| 73 | Cl | Cl  | H   | Me | Me | SCH₂COOEt            | H     | H |
| 74 | I  | I   | I   | Me | Me | Br                   | Br    | H |
| 75 | Cl | Cl  | H   | Me | Me | Br                   | SO₂Et | H |
| 76 | Cl | Cl  | H   | Me | Me | Cl                   | SO₂Et | H |
| 77 | Br | H   | F   | Me | Me | Br                   | Br    | H |
| 78 | Cl | Cl  | I   | Me | Me | Br                   | Br    | H |
| 79 | Cl | CH₃ | H   | Me | Et | Br                   | Br    | H |
| 80 | Cl | Cl  | CH₃ | Me | Et | Br                   | Br    | H |
| 81 | Cl | Br  | H   | Me | Et | Br                   | Br    | H |
| 82 | Cl | Cl  | CH₃ | Me | Et | Br                   | Cl    | H |
| 83 | Cl | Cl  | Cl  | Me | Et | Br                   | Cl    | H |
| 84 | Cl | CH₃ | H   | Me | Et | Br                   | Cl    | H |
| 85 | Cl | Br  | H   | Me | Et | Br                   | Cl    | H |
| 86 | Cl | Cl  | H   | H  | Et | Br                   | H     | H |

The above compounds were prepared as follows:

Example 1

N-(3'-Bromo-1',1'-dimethylacetonyl)-3,5-dichlorobenzamide

N-(1',1'-dimethylpropynyl)-3,5-dichlorobenzamide (40 gm, 0.156 m) was dissolved in methylene chloride (600 ml) and bromine (25 gm, 0.156 m) in methylene chloride (100 ml) was added gradually with stirring at room temperature. After the complete addition of the bromine, the mixture was stirred for another 15 minutes and diluted with hexane (500 ml). The yellowish-white precipitate which formed was filtered and dried to yield 58 gm of 2-(3',5'-dichlorophenyl)-4,4-dimethyl-5-bromomethylenoxaxoline hydrobromide. The oxazoline hydrobromide (55 gm, 0.13 m) was added to concentrated sulfuric acid (200 ml) and stirred to obtain a clear solution. Water (20 ml) was added and the mixture heated at about 50° C. for about 24 hours. The mixture was then poured into ice water (about 2000 ml) and the white precipitate which formed was filtered and dried. Recrystallization from isopropanol, ether and hexane (1:1:2) yielded 21 gm of pure product.

Examples 2–4, 31, 50–53, 56, 61, 65, 67 and 86 were prepared in an analogous manner to the procedure of Example 1.

Example 5

N-(3'-bromo-3'-chloro-1',1'-dimethylacetonyl)3,5-dichlorobenzamide a. 2-(3,5-dichlorophenyl)-4,4-dimethyl-5-chloromethylenyloxazoline N-(1',1'-dimethyl-2'-propynyl)-3,5-dichlorobenzamide (100 gm, 0.39 m) was dissolved in ethyl acetate and chlorine gas was bubbled through it gently with cooling and rapid mixing. The temperature was maintained between 10°–20° C. After about 0.7 equivalent of chlorine was bubbled through it, the resulting white solid was removed by filtration and washed with ethyl acetate and hexane (1:1, 50 ml). The filtrate was diluted with hexane (400 ml) and treated with more chlorine gas as described above, using a total of 22.7 gm chlorine (0.39 m). The white precipitate was removed from this slurry as described above. The combined weight of the product obtained as the hydrochloride salt was 102 gm.

b. 5-bromo-5-bromochloromethyl-4,4-dimethyl-2-(3,5-dichlorophenyl)-oxazoline 2-(3,5-dichlorophenyl)-4,4-dimethyl-5-chloromethylenyloxazoline hydrochloride (0.9 gm, 0.00275 m) was slurried in 20 ml of methylene chloride (20 ml). Bromine (0.9 gm, 0.0056 m) was added to this slurry and the mixture heated to reflux for 1 hour. The resulting yellow-white precipitate was filtered and dried.

c. N-(3'-bromo-3'-chloro-1',1'-dimethylacetonyl)-3,5-dichlorobenzamide

The product from step (b) was dissolved in 25 ml of methanol and 10 ml of 10% (w/w) hydrochloric acid was added. The mixture was heated to and maintained between 40°–50° C. for 1 to 2 hours. After which it was diluted with ice cold water to obtain a white solid which was filtered and dried to yield 0.86 gm of product.

Example 55, 59, 60, 62, 63, 69 and 82–85 were prepared in a manner analogous to Example 5.

Example 6

N-(3',3'-dibromo-1',1'-dimethylacetonyl)-3-bromobenzamide

Bromine (18 gm, 0.113 m) was added gradually over 15 minutes to a solution of N-[3'-(3'-methyl-1'-butyn)]-3,5-dichlorobenzamide (15 gm, 0.056 m) in methylene chloride (100 ml). The mixture was heated to reflux for 2–3 hours, then cooled and poured into 300 ml of hexane. The precipitate which formed was filtered and dried. 5-bromo-5-dibromomethyl-4,4-dinethyl-2-(3',5'-dichlorophenyl) oxazoline hydrobromide (22 gm) was obtained as an intermediate product.

This intermediate product was hydrolyzed using methanol and 10% hydrochloric acid at 40°–50° C. as described in Example 5 to obtain 14 gm of product.

Examples 7–18, 45–52, 57, 58, 64, 68, 71, 72, 74 and 77–81 were prepared in an analogous manner to the procedure of Example 6. Example 18 was about 50 percent pure compound.

Example 19

N-(1',1'-dimethyl-3'-hydroxyacetonyl)-3,5-dichlorobenzamide

N-(1',1'-dimethyl-3'-acetoxyacetonyl)-3,5-dichlorobenzamide (5.0 gm, 0.15 m) was treated with potassium carbonate (0.21 gm, 0.0015 m) in 250 ml methanol at room temperature for 12 hours. The methanol was removed by a vacuum, the residue was taken up in ether and washed successively with saturated sodium bicarbonate, water and brine. Drying of the ether solution followed by removing the solvent yielded 4.0 gm (98%) of pure product.

Example 20

N-(1',1'-dimethyl-3'-methylsulfonyloxyacetonyl)-3,5-dichlorobenzamide

N-(1',1'-dimethyl-3'-hydroxyacetonyl)-3,5-dichlorobenzamide (1.0 gm, 0.00345 m) was dissolved in methylene chloride (25 ml) and diisopropylethylamine (0.44 gm, 0.0035 m) and cooled to about 5° C. under a nitrogen atmosphere. While the solution was stirred magnetically, methanesulfonylchloride (0.475 gm, 0.0041 m) was added dropwise. After its addition, the mixture was stirred about an hour longer while maintaining the temperature at 5°–10° C. The mixture was then poured into ice water (500 ml) containing methylene chloride (100 ml). The organic layer was separated and was washed with cold 1% hydrochloric acid, saturated sodium bicarbonate, water and brine, and then dried over anhydrous potassium carbonate. The solvent was removed and 800 mg of the desired product was obtained.

Example 21

N-(1',1'-dimethyl-3'-methoxyacetonyl)-3,5-dichlorobenzamide

Methyl iodide (30 ml) and freshly prepared silver oxide (0.77 gm, 0.003 m) were added to N-(1',1'-dimethyl-3'-hydroxyacetonyl)-3,5-dichlorobenzamide (0.08 gm, 0.003 m) (Example 45) and the reaction mixture was refluxed for about 10 hours. Then fresh silver oxide (0.7 gm) was added and the mixture was refluxed for another 2 hours. The inorganic salts were removed by filtration, the filter cake was washed with ether and the solvents were stripped off to obtain 0.5 gm of product after recrystallization from ethylacetate and hexane.

Example 22

N-(3'-cyano-1',1'-dimethylacetonyl)-3,5-dichlorobenzamide

N-(3'-chloro-1',1'-dimethylacetonyl)-3,5-dichlorobenzamide (30 gm, 0.0972 m), sodium cyanide (15 gm, 0.306 m) and 18-crown-6 (1 gm) were dissolved in 300 ml of acetonitrile in a round bottom flask under a nitrogen atmosphere. The mixture was heated to reflux for about 4 hours. The contents of the flask were then cooled and transferred to a separatory funnel along with 100 ml of water and 500 ml of methylene chloride and mixed well. The aqueous layer was discarded and the organic layer was washed sequentially with water and brine, dried and the solvents stripped off to yield 12.5 gm of the product after recrystallization from methylene chloride and hexane.

Example 24

N-(3'-thiocyano-1',1'-dimethylacetonyl)-3,5-dichlorobenzamide

N-(3'-bromo-1',1'-dimethylacetonyl)-3,5-dichlorobenzamide (4.0 gm, 0.0113 m) was dissolved in acetone (50 ml) and stirred with potassium thiocyanate (2.2 gm, 0.0226 m) for about 16 hours at room temperature. The inorganic salts were removed by filtration and the solvents were removed under vacuum to obtain 3.20 gm of product which contain less than 5% of its isothiocyanate isomer (Example 23).

Examples 23, 36, 37, 38, 54, 66 and 73 were prepared in a manner analogous to the procedure used for Example 24, although a higher reaction temperature of about 50° C. was used for examples 23, 36 and 38 and DMF was used as a solvent in place of acetone.

Example 25

N-[3'-(N,N-dimethyldithiocarbamoyl-1',1'-dimethylacetonyl)]-3,5-dichlorobenzamide N-(3'-bromo-1',1'-dimethylacetonyl)-3,5-dichlorobenzamide (4.0 gm, 0.011 m) dissolved in 50 ml of acetone was treated with sodium dimethyldithiocarbamate (4.1 gm, 0.022 m) at room temperature for about 12 hours. The inorganics were removed by filtration and the solvent was removed to produce 2.1 gm of the desired product after recrystallization from ether.

Example 26

N-(3',3'-dibromo-3'-cyano-1',1'-dimethylacetonyl)-3,5-dichlorobenzamide

N-(3'-cyano-1',1'-dimethylacetonyl)-3,5-dichlorobenzamide (1.5 gm, 0.005 m) was dissolved in methylene chloride (50 ml) and 5 drops of glacial acetic acid and then bromine (1.6 gm, 0.01 m) were added. The mixture was stirred at room temperature overnight, and then placed in a separatory funnel containing another 10 ml of methylene chloride where it was washed with saturated sodium bicarbonate, water, and brine. The solvent was removed after drying over anhydrous magnesium sulfate to obtain 1.8 gm of desired product.

Example 27

N-(3',3'-dichloro-3'-cyano-1',1'-dimethylacetonyl)-3,5-dichlorobenzamide

N-(3'-cyano-1',1'-dimethylacetonyl)-3,5-dichlorobenzamide (1.5 gm, 0.005 m) was dissolved in 50 ml of methylene chloride and 1.5 gm (0.1 m) of sulfuryl chloride were added. The mixture was heated to reflux for about 2 hours. Upon cooling, a white precipitate was formed which was filtered and dried to yield 1.3 gm of the desired product.

Example 29 was prepared in an analogous manner.

Example 30

N-(3',3'-diiodo-1',1'-dimethylacetonyl)-3,5-dichlorobenzamide 2-(3',5'-dichlorophenyl)-5-iodomethylene-4,4-dimethyloxazolinium iodide (5.0 gm, 0.0098 m) was disolved in methanol (200 ml) and N-chlorosuccinimide (3.3 gm, 0.025 m) was added. The mixture was stirred at room temperature for about 1 hour, then diluted with enough water to obtain a cloudy solution and stirred overnight. The reaction mixture was further diluted with water, then filtered and the solid obtained was dried and recrystallized from a mixture of ethyl acetate and hexane to yield 3.8 gm of the desired product.

Example 33

N-(3'-bromo-3',3'-dichloro-1',1'-dimethylacetonyl)-3,5-dichlorobenzamide

N-(1',1'-dimethylpropynyl)-3,5-dichlorobenzamide (25 gm, 0.096 m) was dissolved in methylene chloride (300 ml) and excess chlorine (2.5–3 equivalents) was bubbled through this solution at room temperature. After the starting material had disappeared (as indicated by thin layer chromatography, TLC), this solution was washed with aqueous sodium sulfite and the solvent was removed. The white solid obtained was slurried in ether (250 ml) and pyridine (8.0 gm) was added. The mixture was stirred for about 1 hour and then filtered to remove solids. The mother liquor was washed sequentially with cold 1% hydrochloric acid (25 ml), sodium bicarbonate (50 ml), water and brine. The solvent was removed after drying over magnesium sulfate and 28 gm of 2-(3',5'-dichlorophenyl)-4,4-dimethyl-5-chloro-5-dichloromethyloxazoline was obtained.

The above prepared oxazoline (5 gm, 0.0138 m) was dissolved in methylene chloride (100 ml) and placed in a round bottom flask equipped with a reflux condenser, magnetic stirrer and a heating mantle. The solution was kept under a nitrogen atmosphere and treated with diazabicyclononane (2.3 gm, 0.0207 m) and heated to reflux for about 2 hours when TLC indicated disappearance of the starting material. The reaction mixture was then transferred to a separatory funnel using an additional 200 ml methylene chloride and washed sequentially with 5% hydrochloric acid, saturated sodium bicarbonate, water and brine. After drying over potassium carbonate, the solvent was removed and 3.6 gm of 2-(3',5'-dichlorophenyl)-4,4-dimethyl-5-dichloromethylenoxazoline was obtained as an oil. The oil was added to 48% hydrobronic acid (10 ml) and bromine (2 ml) and heated to about 50° C. while stirring. After about one-half hour at about 50° C., a yellow precipitate formed which was filtered and washed with water. After drying, 3.0 gm of the desired product was obtained.

Examples 34 and 35 (bromine was used instead of chlorine) were prepared in a manner analogous to Example 33.

Example 39

3-(3',5'-dichlorobenzamido)-3-nethylbutan-2-one-1-azide

N-(3'-bromo-1',1'-dimethylacetonyl)-3,5-dichlorobenzamide (3 gm, 0.0085 m) was dissolved in acetone (100 ml) and sodium azide (1.4 gm, 0.021 m) was added. This mixture was heated to reflux, then cooled in an ice bath after thin layer chromatography indicated no starting materials were present. The mixture was diluted with water (about 200 ml) to obtain a white precipitate which was filtered, washed with water and dried to obtain 2.5 gm of the desired product.

Example 32 was prepared in a manner analogous to Example 26 except only half the amount of bromine was used.

Example 41

N-[1',1'-dimethyl-3'-(1,2,4-triazolyl)acetonyl]-3,5-dichlorobenzamide

N-(3'-bromo-1',1'-dimethylacetonyl)-3,5-dichlorobenzamide (10.0 gm, 0.0283 m) was dissolved in dry acetone (100 ml) and the potassium salt of 1H-1,2,4-triazole (3.1 gm, 0.029 m) was added. The mixture was stirred at room temperature overnight resulting in the formation of a yellow slurry containing a precipitate. The slurry was diluted with a large excess of water (approximately 300 ml). The solid formed was filtered, dried, then slurried in ether and the insoluble material was removed by filtration to obtain 4.5 gm of white solid, the desired product.

Examples 40, 42 and 43 were prepared in an analogous manner to Example 41. Examples 42 and 43 were about 50 percent pure compounds.

Example 44

N-(1',1'-dimethyl-3'-acetoxyacetonyl)-3,5-dichlorobenzamide

N-(1',1'-dimethyl-3'-chloroacetonyl)-3,5-dichlorobenzamide (20 gm, 0.065 m) was dissolved in 100 ml of dry DMF and 10.6 gm (0.128 m) of sodium acetate was added. The slurry was blanketed under a nitrogen atmosphere and then heated to 80°–90° C. for 4 days. The reaction mixture was cooled by adding 100 ml of water. The aqueous solution was extracted four times with 10 ml aliquots of methylene chloride. The combined organic extracts were washed with water (3×100 ml) and brine. The solvent was removed, the resulting white solid dried and then recrystallized from an acetone and hexane (about 1:4) mixture to yield 10.2 gm of the product.

Example 70

N-[3'-(1'-Bromo-1'-fluoro-3'-methyl-2'-oxopentan)]-3,5-dichlorobenzamide

5-Bromomethylen-2-(3',5'-dichlorophenyl)-4-ethyl-4-methyloxazoline (7.97 gm, 0.02 m) was dissolved in methylene chloride and methanol (50 ml, 1:1), and cooled to about −65° C. under a nitrogen atmosphere. Trifluoromethylhypofluorite was bubbled into this solution, intermittently, over a twenty minute time period. Then the reaction mixture was allowed to warm to room temperature and the solvents were removed under vacuum. The residue was dissolved in methanol (75 ml), water (25 ml) and concentrated hydrochloric acid (10 ml) and heated to about 50° C. The white precipitate which appeared in about 30 minutes was filtered, washed with water and dried. Recrystallization from ether and hexane (1:14) resulted in 4.8 gm of product.

Example 75

1-Bromo-3-(3',5'-Dichlorobenzoylamino)-2-oxo-3-methylbutyl ethyl sulfone

N-(3'-Ethylthio-1',1'-dimethylacetonyl)-3,5-dichlorobenzamide (5.0 gm, 0.015 m) was taken in chloroform (200 ml) and meta-chloroperbenzoic acid (7.8 gm, 0.045 m) was added with stirring at room temperature for about 16 hours. The reaction mixture was transferred, with the use of ether (200 ml) as a rinse, to a separatory funnel. The organic solution was washed sequentially with sodium sulfite (2×100 ml), sodium bicarbonate (200 ml), water (100 ml) and brine (200 ml). The solvent was removed after drying over anhydrous sodium sulfate. Recrystallization using ethyl acetate and hexane (1:4) afforded 4.3 gm of 3-(3',5'-dichlorobenzoylamino)-2-oxo-3 -methylbutyl ethyl sulfone. A portion of this sulfone (1.00 gm, 0.0027 mole) was taken in methylene chloride (50 ml) and bromine (0.13 ml, 0.003 mole) was added in one portion. Another 2–3 drops of bromine were added and the mixture was heated to reflux for about 1 hour. The solvent was removed and the resulting oil was recrystallized from hexane to obtain 800 mg of the desired product.

Example 76 was prepared in an analogous manner to Example 75.

Analyses of these examples are presented in Table 4 as their elemental analysis or NMR spectra using tetramethylsilane as a standard.

TABLE 4

| Example | Elemental Analysis, Calculated (Found) or NMR |
|---|---|
| 1 | δ(CDCl$_3$ + DMSO-d$_6$): 7.8, d, J = 2Hz, 2H; 7.5, t, J = 2Hz, 1H;, 7.0, br, 1H; 4.3, S, 2H; 1.7, S, 6H. |

TABLE 4-continued

| Example | Elemental Analysis, Calculated (Found) or NMR |
|---|---|
| 2 | δ(CDCl$_3$ + DMSO-d$_6$): 7.9–7.4, m, 3H; 7.2, br, 1H; 4.4, S, 2H, 1.7, S, 6H. |
| 3 | δ(CDCl$_3$): 7.8–7.2, m, 4H; 7.7, br, 1H; 4.2, S, 2H; 2.4, S, 3H; 1.6, S, 6H. |
| 4 | C = 49.68(48.57), H = 5.09(4.95), N = 4.46(4.55), Br = 25.48(26.55). |
| 5 | δ(CDCl$_3$ + DMSO-d$_6$): 9.0, br, 1H; 8.0, d, 2H; 7.6, t, 1H, 6.7, S, 1H; 1.7, S, 6H. |
| 6 | δ(CDCl$_3$ + DMSO-d$_6$): 9.0, br, 1H; 8.0, d, 2H; 7.7, t, 1H; 6.7, S, 1H; 1.7, S, 6H. |
| 7 | δ(CDCl$_3$ + DMSO-d$_6$): 8.0, br, 1H; 7.8–6.8, m, 5H; 6.65, S, 1H; 1.7, S, 6H. |
| 8 | δ(CDCl$_3$): 8.4, br, 1H; 8.3–7.4, m, 4H; 6.8, S, 1H; 1.8, S, 6H. |
| 9 | δ(CDCl$_3$ + DMSO-d$_6$): 8.75, br, 1H; 8.1–7.15, m, 4H; 6.7, S, 1H; 1.7, S, 6H. |
| 10 | δ(CDCl$_3$ + DMSO-d$_6$): 9.0, br, 1H; 8.2–7.5, m, 4H; 6.7, S, 1H; 1.7, S, 6H. |
| 11 | δ(CDCl$_3$): 7.9–7.3, ABQ, 4H; 7.2, br, 1H; 6.7, S, 1H; 2.4, S, 3H; 1.7, S, 6H. |
| 12 | δ(CDCl$_3$): 7.9–6.9, ABQ, 4H; 7.1, br, 1H; 6.7, S, 1H; 3.8, S, 3H; 1.7, S, 6H. |
| 13 | C = 32.36(31.65), H = 2.70(2.64), N = 3.15(2.96), S = 7.19(7.53), F = 4.27(4.27), Br = 35.96(34.78). |
| 14 | C = 41.41(41.44), H = 4.01(3.98), N = 3.71(3.69), Br = 42.38(42.32). |
| 15 | C = 29.45(29.62), H = 2.74(2.52), N = 2.86(2.76), Br = 32.68(32.91), I = 25.95(26.24). |
| 16 | δ(CDCl$_3$): 8.5, br, 1H; 7.5, m, 2H; 7.25, m, 1H; 6.7, S, 1H; 2.4, S, 6H; 1.7, S, 6H. |
| 17 | C = 33.33(32.60), H = 2.55(2.49), N = 3.24(3.19), Br = 37.04(38.34). |
| 19 | δ(CDCl$_3$ + DMSO-d$_6$): 9.0, br, 1H; 7.8, d, 2H; 7.4, t, 1H; 4.4, S, 2H; 1.5, S, 6H. |
| 20 | δ(CDCl$_3$ + DMSO-d$_6$): 9.2, br, 1H; 8.0, d, 2H; 7.6, t, 1H; 5.15, S, 2H; 3.15, S, 3H; 1.5, S, 6H. |
| 21 | C = 51.33(51.17), H = 4.97(4.87), N = 4.60(4.87), Cl = 23.31(23.20). |
| 22 | C = 52.19(50.68), H = 4.04(4.00), N = 8.36(8.56), Cl = 23.70(22.43). |
| 23 | δ(CDCl$_3$): 9.2, br, 1H; 8.1, d, 2H; 7.8, t, 1H; 4.55, S, 2H; 1.5, S, 6H. IR (Nujol): 3350, 2150, 1650 cm$^{-1}$. |
| 24 | δ(CDCl$_3$): 9.2, br, 1H; 8.0, d, 2H; 7.7, t, 1H · 4.5, S, 2H; 1.5, S, 6H. IR (Nujol): 3350, 2075, 1650 cm$^{-1}$. |
| 25 | δ(CDCl$_3$): 7.8, d, 2H; 7.6, t, 1H; 7.4, br, 1H; 4.75, S, 2H; 3.5, two S, 6H; 1.8, S, 6H. |
| 26 | δ(CDCl$_3$ + DMSO-d$_6$): 9.6, br, 1H; 7.9, d, 2H; 7.4, t, 1H; 1.75, S, 6H. |
| 27 | C = 42.42(40.06), H = 2.74(2.72), N = 7.61(7.21), Cl = 35.53(35.56). |
| 28 | C = 50.30(49.20), H = 5.13(4.92), N = 4.19(4.21), Cl = 21.21(22.46), S = 9.59(9.43). |
| 29 | δ(CDCl$_3$): 7.6, d, 2H; 7.44, t, 1H; 7.2, br, 1H; 3.1–2.7, Q, 2H; 1.7, S, 6H; 1.50–1.2, t, 3H. |
| 30 | δ(CDCl$_3$ + DMSO-d$_6$): 8.5, br, 1H; 7.9, d, 2H; 7.5, t, 1H; 6.1, S, 1H; 1.8, S, 6H. |
| 31 | δ(CDCl$_3$ = DMSO-d$_6$): 9.0, br, 1H; 7.7, d, 2H; 7.6, t, 1H; 4.2, S, 2H; 1.8, S, 6H. |
| 32 | δ(CDCl$_3$ + Acetone-d$_6$): 8.5, br, 1H; 7.8, m, 2H; 7.5, m, 3H; 5.7, S, 1H; 1.75 and 1.7, two S, 6H. |
| 33 | C = 34.16(34.39), H = 2.39(2.63), N = 3.32(3.31), Cl = 33.61(34.28), Br = 18.94(19.03). |
| 34 | C = 28.21(29.33), H = 1.97(2.34), N = 2.75(2.80), Cl = 13.88(13.19), Br = 46.93(40.94). |
| 35 | δ(Acetone-d$_6$ + DMSO-d$_6$): 9.0, br, 1H; 7.9, m, 3H; 1.65, S, 6H. |
| 36 | C = 53.95(53.76), H = 4.03(3.93), N = 3.49(3.46), Cl = 26.54(26.02). |
| 37 | C = 57.58(57.38), H = 4.79(4.82), N = 3.54(3.45), S = 8.08(8.24), Cl = 17.93(18.23). |
| 38 | C = 42.18(41.84), H = 4.52(4.56), N = 8.20(8.10), S = 25.02(25.72), Cl = 13.83(14.74). |
| 39 | C = 45.73(45.18), H = 3.84(3.87), N = 17.78(16.45), Cl = 22.50(23.45). |
| 40 | C = 47.07(46.69), H = 3.70(3.20), CN = 24.01(23.04), Cl = 17.37(18.41). |
| 41 | C = 49.28(49.31), H = 4.14(4.08), Cl = 20.78(22.06), N = 16.42(15.78). |
| 44 | δ(CDCl$_3$ + DMSO-d$_6$): 9.0, br, 1H; 8.0, d, 1H; 7.6, t, 1H; 4.9, S, 2H; 2.1, S, 3H; 1.5, S, 6H. |
| 45 | C = 33.37(33.63), H = 2.57(2.61), N = 3.24(3.27), Br = 37.0(36.6), Cl = 16.41(16.53). |
| 46 | C = 35.01(35.00), H = 2.57(2.61), N = 3.24(3.27), Cl = 15.90(15.79), Br = 35.83(35.63). |
| 47 | C = 38.00(39.36), H = 3.61(3.60), N = 2.95(2.37), Cl = 14.96(14.94), Br = 33.71(34.21). |
| 48 | C = 36.56(37.36), H = 3.29(3.46), N = 3.04(3.21), Br = 34.74(33.86), Cl = 15.41(15.20). |
| 49 | C = 44.10(44.90), H = 4.20(3.83), N = 3.67(3.63), Cl = 18.64(20.49), Br = 21.00(22.91). |
| 50 | C = 36.56(34.88), H = 3.29(3.24), N = 3.04(2.76), Br = 34.74(31.21). |
| 51 | C = 38.01(38.08), H = 3.61(3.50), N = 2.95(3.38), Br = 33.08(29.11), Cl = 16.96(17.08). |
| 52 | C = 39.38(39.25), H = 3.92(3.64), N = 2.87(2.46), Br = 32.74(33.35). |
| 53 | C = 42.53(41.07), H = 3.84(3.72), N = 3.81(3.52), Br = 21.77(20.99). |
| 54 | C = 48.70(48.80), H = 4.09(3.89), N = 8.11(7.85), Br = 20.54(20.87), S = 9.29(9.27). |
| 55 | C = 38.85(39.03), H = 3.24(3.38), N = 3.49(3.61), Cl = 26.53(26.30), Br = 19.93(19.73), O = 7.97(7.79). |
| 56 | C = 46.94(47.74), H = 4.55(4.51), N = 4.21(4.16), Cl = 10.66(11.38). |
| 57 | C = 37.94(37.43), H = 3.43(3.15), N = 3.04(3.26), Cl = 8.61(8.00), Br = 38.84(36.87). |
| 58 | C = 34.24(32.09), H = 3.09(2.96), N = 3.07(2.91), Br = 52.58(54.54). |
| 59 | C = 36.26(36.01), H = 3.04(3.16), N = 3.52(3.44), Br = 40.21(38.11). |
| 60 | C = 37.94(38.44), H = 3.43(3.47), N = 3.40(3.45), Br = 38.84(38.71), Cl = 8.62(8.76). |
| 61 | C = 41.40(41.22), H = 4.01(4.10), N = 3.71(3.72), Br = 42.39(43.17). |
| 62 | C = 32.42(32.03), H = 2.72(2.64), N = 3.15(3.11), Cl = 9.99(9.99), Br = 18.00(16.43), I = 28.55(28.66). |
| 63 | C = 42.82(41.86), H = 3.59(3.59), N = 4.16(4.03), Br = 23.74(21.4), F = 5.64(5.43). |
| 64 | C = 43.69(43.98), H = 3.64(3.69), N = 3.92(3.95), Cl = 39.76(39.70). |
| 65 | C = 44.34(41.07), H = 3.72(3.73), N = 3.70(3.66), Br = 21.08(20.98). |
| 66 | C = 50.43(47.57), H = 3.95(4.04), N = 7.84(7.25), Cl = 19.85(20.00), S = 8.98(8.72). |
| 67 | C = 45.83(44.55), H = 4.10(4.13), N = 3.56(3.66), Br = 20.33(19.82). |
| 68 | C = 38.17(37.02), H = 3.20(3.35), N = 2.97(3.13), Br = 33.86(35.74), Cl = 15.02(15.20). |
| 69 | C = 40.66(39.30), H = 3.17(3.41), N = 3.39(3.53), Br = 19.32(19.59), Cl = 25.72(26.00). |
| 70 | δ(Acetone-d$_6$): 7.84, d, 2H; 7.68, m, 1H; 7.6, br, 1H; 7.3, d, J = 48 Hz, 1H; 2.25–2.0, m, 2H; 1.6, S, 3H; 1.1–0.9, t, 3H. $^{19}$F-NMR (CDCl$_3$): -151.5, d, J = 48 Hz, 1F (CCl$_3$F internal standard). |
| 71 | C = 32.47(32.55), H = 2.50(2.57), N = 2.91(2.84), Br = 33.30(33.32), Cl = 22.16(22.43). |
| 72 | C = 34.66(34.91), H = 2.65(2.75), N = 3.37(3.22), Br = 38.51(37.60), F = 4.57(4.62). |
| 73 | C = 48.99(47.97), H = 4.88(5.17), N = 3.57(3.59), Cl = 18.07(18.42), S = 8.17(7.82). |
| 74 | C = 19.46(19.66), H = 1.36(1.48), N = 1.89(1.94), I = 51.40(51.94), Br = 21.57(19.99). |
| 75 | C = 37.78(38.03), H = 3.62(3.78), N = 3.15(3.25), Cl = 15.93(16.15), Br = 17.95(18.06). |
| 76 | C = 41.96(42.07), H = 4.02(4.07), N = 3.50(3.50), Cl = 26.58(26.85), S = 8.00(7.81). |

TABLE 4-continued

| Example | Elemental Analysis, Calculated (Found) or NMR |
|---|---|
| 77 | C = 31.34(31.25), H = 2.41(2.49), N = 3.05(3.11), Br = 52.12(51.94), F = 4.13(4.15), O = 6.96(7.16). |
| 78 | C = 25.84(26.03), H = 1.81(1.86), N = 2.51(2.45), Br = 28.65(29.08), C1 = 12.71(13.43), I = 22.75(21.64), O = 5.74(5.45). |
| 79 | C = 39.51(38.23), H = 3.79(3.70), N = 3.29(3.17), Br = 37.55(38.05). |
| 80 | C = 36.56(36.74), H = 3.29(3.31), N = 3.05(3.01), O = 6.96(7.28), Br = 34.74(32.79), C1 = 15.42(16.92). |
| 81 | C = 33.47(31.68), H = 2.61(2.66), N = 2.79(2.65), Br = 47.71(47.90), C1 = 7.06(7.78). |
| 82 | $\delta(CDCl_3)$: 7.65, S, 2H,; 6.8, br, 1H; 6.5, S, 1H; 2.5, S, 3H; 2.4–1.95, m, 2H; 1.7, S, 3H; 1.0–0.8, t, 3H. |
| 83 | $\delta(CDCl_3 + Acetone-d_6)$: 7.7, S, 2H; 6.8, br, 1H; 6.5, S, 1H; 2.4–2.0, m, 2H; 1.76, S, 3H; 1.1–0.9, t, 3H. |
| 84 | $\delta(CDCl_3)$: 7.5–7.2, m, 3H; 6.7, br, 1H; 6.5, S, 1H; 2.4, S, 3H; 2.4–2.0, m, 2H; 1.76, S, 3H; 1.1–0.9, t, 3H. |
| 85 | $\delta(CDCl_3)$; 8.0–7.6, m, 4H (including 1H for NH); 6.65, S, 1H; 2.3–2.0, m, 2H; 1.7, S, 3H; 1.2–0.95, t, 3H. |
| 86 | C = 40.83(40.70), H = 3.43(3.45), N = 3.97(3.84), Br = 22.63(20.79), C1-20.08(20.56). |

Example 87

The compounds of Examples 1–57 were tested for their fungicidal activity. The compounds were tested in vivo against cucumber downy mildew (*Pseudoperonospora cubensis*) and tomato late blight (*Phytophthora infestans*) and in vitro against *Pythium ultimum* and *Phytophthora capsici*.

A. Cucumber Downy Mildew (CDM)

*Pseudoperonospora cubensis* was maintained on leaves of live cucumber plants in a constant temperature room at about 65° to 75° F. in humid air with moderate light intensity for 7 to 8 days. A water suspension of the spores from infested leaves was obtained and the spore concentration was adjusted to about $1 \times 10^5$ spores per milliliter (ml).

Marketer cucumber seedlings were selected at their one to two true leaf stage and thinned to one plant (or two leaves) per pot. The seedlings were sprayed to runoff with a solution of a test compound comprising 300 ppm of the active ingredient of the test compound in a 2:1:1 mixture of water, acetone and methanol. After drying, a spore suspension of cucumber downy mildew was applied to the lower surface of the plant leaves with a DeVilbiss atomizer until fine droplets were visible on the leaves. The inoculated seedlings were placed in a humidity cabinet for 24 hours at 65° to 75° F. and then placed into a controlled temperature room. Treatment evaluations were made 7 to 8 days after inoculation. The results are reported in Table 3 as the percent disease control and represent the level of disease suppression when compared to the untreated control plants present at spraying and inoculation that was dark green, not yellow, compared to the untreated control leaves.

B. Tomato Late Blight (TLB)

*Phytophthora infestans* was maintained on 6 to 8 inch tall Rutgers tomato seedlings for 4 to 5 days in a constant temperature humidity chamber at 65° to 75° F. with moderate light intensity. A water suspension of the spores from infested plants was obtained and the spore concentration was adjusted to about $1 \times 10^5$ spores per ml.

Rutgers tomato seedlings, 3 to 5 inches tall, were fertilized with a water-soluble fertilizer to promote rapid succulent growth. About 4 to 5 days later, the seedlings were sprayed to runoff with a solution of a test compound comprising 300 ppm of the active ingredient of the test compound in a 2:1:1 mixture of water, acetone and methanol. After drying, the tomato late blight spore suspension was applied to the lower leaf surface of the plant leaves with a DeVilbiss atomizer until fine droplets were visible on the leaves. The inoculated seedlings were placed in a humidity cabinet at 65° to 70° F. for 24 hours and then moved to a controlled temperature humidity chamber until treatment evaluations were made about 5 to 7 days after inoculation. The results are reported in Table 3 as percent disease control which represents the percentage of the treated plants (leaves and stems) lacking of disease signs or symptoms when compared to untreated control plants.

C. In Vitro Tests

In vitro testing was done to determine the effects of the test compounds on the mycelial growth of *Pythium ultimum* and *Phytophthora capsici*. Corn meal agar was autoclaved for 15 minutes and agar suspensions containing a concentration of each test compound at 100 ppm (based on weight to weight). The agar was poured into petri dishes and allowed to harden. Thereafter, 6 mm, circular mycelial fungal plugs of 1 week old stock culture grown on amended corn meal agar were placed on the surface of the agar in the petri dishes. The dishes were incubated under light at room temperature, about 22° C., for two days (*P. ultimum*) and three days (*P. capsici*) until the colonies in the control dishes had grown about half or more of the diameter of the petri dish. The control dishes consisted of corn meal agar amended with 2 ml of acetone, the solvent used for the test compounds. The diameter (mm) of the mycelial growth in each dish was measured. The results are reported in Table 3 as percent growth inhibition calculated from the measured colony diameters of the control colonies and colonies grown in the presence of test compounds as follows:

$$\text{Percent Growth Inhibition} = \frac{\text{Dia. of Control Growth (mm)} - \text{Dia. of Test } Cpd. \text{ Growth (mm)}}{\text{Diameter Control Growth (mm)}} \times 100$$

TABLE 5

| | In Vivo (300 ppm) | | In Vitro (100 ppm) | |
|---|---|---|---|---|
| Example | CDM | TLB | P. ultimum | P. capsici |
| 1 | 100 | 100 | 99 | 100 |
| 2 | 0 | 0 | 72 | 44 |
| 3 | 100 | 80 | 100 | 100 |
| 4 | 75 | 80 | 100 | 75 |
| 5 | 100 | 100 | 99 | 85 |
| 6 | 100 | 100 | 97 | 82 |
| 7 | 90 | 90 | 99 | 100 |
| 8 | 95 | 100 | 100 | 100 |
| 9 | 99 | 40 | 100 | 100 |
| 10 | 100 | 95 | 99 | 88 |
| 11 | 99 | 0 | 100 | 100 |
| 12 | 99 | 20 | 100 | 100 |
| 13 | 80 | 90 | 62 | 78 |
| 14 | 80 | 10 | 100 | 100 |
| 15 | 80 | 20 | 100 | 100 |
| 16 | 98 | 40 | 97 | 100 |
| 17 | 45 | 70 | 99 | 100 |
| 18 | 50 | 20 | 90 | 100 |
| 19 | 0 | 0 | 86 | 50 |
| 20 | 100 | 100 | 100 | 90 |
| 21 | 0 | 0 | 71 | 41 |
| 22 | 0 | 0 | 75 | 60 |
| 23 | 100 | 100 | 100 | 100 |

TABLE 5-continued

| | In Vivo (300 ppm) | | In Vitro (100 ppm) | |
|---|---|---|---|---|
| Example | CDM | TLB | P. ultimum | P. capsici |
| 24 | 100 | 95 | 100 | 100 |
| 25 | 95 | 0 | 62 | 90 |
| 26 | 0 | 0 | 100 | 100 |
| 27 | 99 | 0 | 93 | 77 |
| 28 | 100 | 98 | 97 | 100 |
| 29 | 95 | 99 | 97 | 86 |
| 30 | 99 | 40 | 100 | 100 |
| 31 | 95 | 80 | 99 | 100 |
| 32 | 90 | 10 | 90 | 100 |
| 33 | 80 | 0 | 100 | 80 |
| 34 | 60 | 70 | 100 | 90 |
| 35 | 0 | 0 | 80 | 40 |
| 36 | 90 | 70 | 20 | 20 |
| 37 | 100 | 0 | 20 | 20 |
| 38 | 80 | 80 | 50 | 60 |
| 39 | 90 | 20 | 100 | 100 |
| 40 | 80 | 95 | 100 | 50 |
| 41 | 100 | 70 | 100 | 90 |
| 42 | 100 | 0 | 100 | 100 |
| 43 | 95 | 60 | 100 | 30 |
| 44 | 40 | 10 | 90 | 50 |
| 45 | 80 | 95 | 100 | 100 |
| 46 | 100 | 95 | 100 | 100 |
| 47 | 50 | 80 | 73 | —* |
| 48 | 0 | 0 | 17 | 22 |
| 49 | 80 | 0 | 11 | 34 |
| 50 | 95 | 0 | 60 | 83 |
| 51 | 20 | 20 | 10 | 49 |
| 52 | 10 | 10 | 0 | 43 |
| 53 | 30 | 100 | 100 | 100 |
| 54 | 90 | 100 | 100 | 90 |
| 55 | 100 | 100 | 100 | 100 |
| 56 | 100 | 95 | 100 | 100 |
| 57 | 100 | 80 | 100 | 100 |
| 58 | 95** | 0** | 100 | 100 |
| 59 | 90** | 0** | 100 | 100 |
| 60 | 100** | 100** | 100 | 100 |
| 61 | 99** | 20** | 100 | 100 |
| 62 | 0** | 0** | 100 | 100 |
| 63 | 20** | 0** | 100 | 100 |
| 64 | 100** | 100** | 100 | 100 |
| 65 | 95** | 0** | 100 | 100 |
| 66 | 0** | 0** | 86 | 90 |
| 67 | 40** | 0** | 95 | 92 |
| 68 | 60** | 10** | 100 | 78 |
| 69 | 99** | 0** | 100 | 100 |
| 70 | 100** | 100** | — | — |
| 71 | 100** | 95** | 91 | 70 |
| 72 | 100** | 100** | 100 | 100 |
| 73 | 95** | 0** | 100 | 100 |
| 74 | 85** | 0** | 100 | 100 |
| 75 | 30 | 0 | 100 | 86 |
| 76 | 0 | 0 | 56 | 45 |
| 77 | 90** | 0** | 100 | 100 |
| 78 | 95** | 0** | 97 | 78 |
| 79 | 100** | 100** | 80 | 100 |
| 80 | 100** | 95** | 53 | 38 |
| 81 | 100** | 80** | 72 | 72 |
| 82 | 100** | 100** | 100 | 31 |
| 83 | 100** | 100** | 32 | 29 |
| 84 | 100** | 100** | 100 | 100 |
| 85 | 100** | 100** | 100 | 100 |
| 86 | 100 | 95 | 99 | 95 |

\* - Not tested.
\*\* - Values reported at 200 ppm.

Example 88

The phytotoxic effects of three compounds of the prior art, N-(1',1'-dimethyl-3'-chloroacetonyl)-3,5-dichlorobenzamide (compound A), N-(1',1'-dimethyl-3'-chloroacetonyl)-3-chlorobenzamide (compound B) and N-(1',1'-dimethyl-3'-chloroacetonyl)-3-chloro-5-fluorobenxamide (compound C) and several of the compounds utilized in the present invention (identified by numbers which correspond to the preceding Examples) were determined by measuring the inhibition in height growth of cucumber and tomato plants.

The height of all the plants was measured and then test compounds were applied to the plant by an overhead sprayer. The test compounds were prepared in a solvent of 1:1:2 mixture of acetone:methanol:water to provide concentrations of 150, 300, 600 and 1200 ppm of active ingredient. Additionally, the height of control plants was measured and these plants were treated with the solvent mixture. After the spray was dry, all plants were placed in humidity cabinets at a temperature of 65° to 75° F. for 24 hours and then the tomato plants were placed on a greenhouse bench at room temperature, about 22° C., and the cucumber plants were placed in a nonhumid cabinet in a controlled temperature room at 65° to 75° F. All of the plants were subirrigated.

After 7 days (cucumber) or 10 days (tomato), height was again measured. The test compound dosage required to cause a 10 or 25% inhibition of growth was determined by comparing the average growth of the untreated controls with that of the treated plants and by correlating the growth response with the chemical dosage using regression analysis techniques. The results are given in Table 6.

TABLE 6

| | | Amount of Compound (ppm) Required to Inhibit Growth | |
|---|---|---|---|
| Compound | % Inhibition | Cucumber | Tomato |
| A | 10 | 565 | 1,316 |
| | 25 | 953 | 2,491 |
| B | 10 | 217 | 1,234 |
| | 25 | 523 | 2,241 |
| C | 10 | 504 | 151 |
| | 25 | 937 | 411 |
| 1 | 10 | >10,000 | >10,000 |
| | 25 | >10,000 | >10,000 |
| 6 | 10 | >10,000 | >10,000 |
| | 25 | >10,000 | >10,000 |
| 9 | 10 | >10,000 | >10,000 |
| | 25 | >10,000 | >10,000 |
| 16 | 10 | 260 | >10,000 |
| | 25 | 537 | >10,000 |
| 31 | 10 | 432 | >10,000 |
| | 25 | 759 | >10,000 |

Example 89

The in vitro activity of two of the prior art compounds, Compound A described in Example 88 and N-(1'-methyl-1'-ethyl-3'-chloroacetonyl)-3,5-dichlorobenzamide (compound D) and several of the compounds utilized in the present invention, whose numbers correspond to the preceding Example numbers, were tested against *Fusarium roseum* and *Pellicularia fillamentosa*. The in vitro test consisted of autoclaving of Difco potato dextrose agar, allowing the agar to cool for about fifteen minutes and then adding sufficient amounts of the test compounds suspended in methanol to obtain 0.1, 1, 10 and 100 ppm concentrations. The agar, containing varied concentrations of the test compounds, was poured into separate petri dishes and allowed to harden. Two discs of mycelia were placed near the edges of each petri dish and the bioassay fungus was grown under light and at room temperature until the radial growth of the control fungus measured 10 to 30 mm. The control dishes consisted of two fungal mycelial discs grown on agar amended only with methanol. The amount of test compound needed to inhibit growth fungal growth by 50 percent is reported in Table 7 as an $EC_{50}$ value. The $EC_{50}$ values were extrapolated from a logarithmic plot of the percent inhibition of growth, compared to the control caused, by a test compound at concentrations of 0.1, 1, 10 and 100 ppm.

It is seen that the compounds utilized in the present invention are from 30 to about 175 times more active against Fusarium and from 6 to about 2200 times more active against Pellicularia than the prior art compounds.

TABLE 7

| Compound | $EC_{50}$ (ppm) | |
|---|---|---|
| | Fusarium roseum | Pellicularia fillamentosa |
| A | 1121 | 44 |
| D | 3152 | 2900 |
| 1 | 36 | 7.6 |
| 5 | 21 | 1.9 |
| 6 | 26 | 0.09 |
| 33 | 18 | 0.9 |

Example 90

The compound of Example 1 and compound A of the prior art were tested for curative activity against tomato late blight (*Phytophthora infestans*). The test was identical to the procedure used in Example 87 for tomato late blight except the plants were inoculated with the fungal spores 24 hours prior to treating the plants with the test compounds. After drying, the plants were placed in a humidity cabinet in a controlled temperature room as described in Example 87. The percent disease control reported in Table 8 was determined about 5 days after inoculation.

TABLE 8

| Compound | Active Ingredient (ppm) | % Curative Disease Control |
|---|---|---|
| A | 6 | 0 |
| | 25 | 0 |
| | 100 | 0 |
| 1 | 6 | 0 |
| | 25 | 15 |
| | 100 | 53 |

What is claimed is:

1. A compound of the formula:

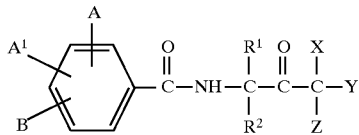

wherein:
A is a chloro, bromo, fluoro, iodo, trifluoromethyl, trifluoromethoxy, fluorosulfonyl, methyl, ethyl, phenyl, methoxy, chloromethyl, $(C_1-C_2)$ alkoxycarbonyl, cyano or hydroxy group;

$A^1$ and B are each independently selected from the group consisting of hydrogen, chloro, bromo, fluoro and methyl group;

X is bromo, iodo, fluoro, cyano, thiocyano, isothiocyano, methylsulfonyloxy, thio$(C_1-C_2)$alkyl, $(C_1-C_2)$alkoxy, carbamoyloxy of the formula (—OC(O)N($R^3$)$_2$), thiocarbamoylthio of the formula (—SC(S)N($R^3$)$_2$), hydroxy, azide, $(C_1-C_4)$alkylcarbonyloxy, phenylcarbonyloxy, phenoxy, phenylthio, trifluoromethylcarboxy, $(C_1-C_3)$alkylthioacetyl, imidazolyl or triazolyl group; and when X is a phenylcarbonyloxy, phenoxy or phenylthio substituent, the phenyl moiety may be substituted with one substituent selected from the group consisting of chloro, fluoro, bromo, iodo or methyl group;

Y and Z are each independently a hydrogen, bromo, chloro, iodo, fluoro, cyano, thiocyano, isothiocyano, methylsulfonyloxy, thio$(C_1-C_2)$alkyl, $(C_1-C_2)$alkoxy, carbamoyloxy of the formula (—OC(O)N($R^3$)$_2$), hydroxy, azide or $(C_1-C_4)$alkylcarbonyloxy group and either, but not both, Y or Z may be an imidazolyl or triazolyl group;

provided when X and Y are halogens and Z is hydrogen or X, Y and Z are all halogens, then the halogens are all the same halogen;

further provided that when
X is cyano, thiocyano, isothiocyano, methylsulfonyloxy, thio$(C_1-C_2)$alkyl, $(C_1-C_2)$ alkoxy, carbamoyloxy of the formula (—OC(O)N ($R^3$)$_2$), thiocarbamoylthio of the formula (—SC(S) N($R^3$)$_2$), azide, $(C_1-C_4)$alkylcarbonyloxy, phenylcarbonyloxy, phenoxy, phenylthio, trifluoromethylcarboxy, imidazolyl or triazolyl group; and when X is a phenylcarbonyloxy, phenoxy or phenylthio substituent, the phenyl moiety may be substituted with one substituent selected from the group consisting of chloro, fluoro, bromo, iodo or methyl group;

Y and Z are not a hydrogen, cyano, thiocyano, isothiocyano, methylsulfonyloxy, thio$(C_1-C_2)$alkyl, $(C_1-C_2)$alkoxy, carbamoyloxy of the formula (—OC (O)N($R^3$)$_2$), azide $(C_1-C_4)$alkylcarbonyloxy, imidazolyl, or triazolyl group;

$R^1$ and $R^2$ are each independently a hydrogen atom or a $(C_1-C_6)$alkyl group; and each $R^3$ is independently a hydrogen or a $(C_1-C_4)$alkyl group.

2. The compound of claim 1, wherein:
A is a chloro, bromo, fluoro, trifluoromethyl, fluorosulfonyl, methyl, ethyl, or methoxy group;

$A^1$ and B are each independently selected from the group consisting of hydrogen, chloro, bromo, fluoro and methyl group;

X is bromo, iodo, fluoro, cyano, thiocyano, isothiocyano, methylsulfonyloxy, thio$(C_1-C_2)$alkyl, $(C_1-C_2)$alkoxy, carbamoyloxy of the formula (—OC(O)N($R^3$)$_2$), thiocarbamoylthio of the formula (—SC(S)N($R^3$)$_2$), hydroxy, azide, $(C_1-C_4)$alkylcarbonyloxy, phenylcarbonyloxy, phenoxy, phenylthio, imidazolyl or triazolyl group; and when X is a phenylcarbonyloxy, a phenoxy or phenylthio substituent, the phenyl moiety may be substituted with one substituent selected from the group consisting of chloro, fluoro, bromo, iodo or methyl group;

Y and Z are each independently a hydrogen, bromo, chloro, iodo, fluoro, cyano, thiocyano, isothiocyano, methylsulfonyloxy, thio$(C_1-C_2)$alkyl, $(C_1-C_2)$alkoxy, carbamoyloxy of the formula (—OC(O)N($R^3$)$_2$), hydroxy, azide or $(C_1-C_4)$alkylcarbonyloxy group and either, but not both, Y or Z may be an imidazolyl or triazolyl group;

provided when X and Y are halogens and Z is hydrogen or X, Y and Z are all halogens, then the halogens are all the same halogen;

further provided that when

X is cyano, thiocyano, isothiocyano, methylsulfonyloxy, thio($C_1$–$C_2$)alkyl, ($C_1$–$C_2$) alkoxy, carbamoyloxy of the formula (—OC(O)N($R^3$)$_2$), thiocarbamoylthio of the formula (—SC(S) N($R^3$)$_2$), azide, $C_1$–$C_4$)alkylcarbonyloxy, phenylcarbonyloxy, phenoxy, phenylthio, imidazolyl or triazolyl group; and when X is a phenylcarbonyloxy, phenoxy or phenylthio substituent, the phenyl moiety may be substituted with one substituent selected from the group consisting of chloro, fluoro, bromo, iodo or methyl group;

Y and Z are not a hydrogen, cyano, thiocyano, isothiocyano, methylsulfonyloxy, thio($C_1$–$C_2$)alkyl, ($C_1$–$C_2$)alkoxy, carbamoyloxy of the formula (—OC(O)N($R^3$)$_2$), azide, ($C_1$–$C_2$)alkylcarbonyloxy, imidazolyl, or triazolyl group;

$R^1$ and $R^2$ are each independently a hydrogen atom or a ($C_1$–$C_6$)alkyl group; and each $R^3$ is independently a hydrogen or a ($C_1$–$C_4$)alkyl group.

3. The compound of claim 2, wherein the A and A1 substituents are at the 3-, 4- or 5-position of the phenyl ring; the A substituent is a chloro, bromo, trifluoromethyl, fluoro or methyl group; the A1 and B substituents are each independently hydrogen, chloro, bromo or fluoro group; $R^1$ and $R^2$ are each independently ($C_1$–$C_4$)alkyl group; X is bromo, iodo, methylsulfonyloxy, thio($C_1$–$C_2$)alkyl, isothiocyano or thiocyano group; Y is a hydrogen, bromo, chloro, cyano or iodo group; and Z is a hydrogen, chloro or bromo group.

4. The compound of claim 3, wherein the A substituent is a chloro, bromo, fluoro or trifluoromethyl group; $A^1$ is a hydrogen, chloro, bromo, fluoro or methyl group; B is a hydrogen atom; $R^1$ and $R^2$ are each independently a ($C_1$–$C_2$) alkyl group; X is a bromo, iodo, methylsulfonyloxy, an isothiocyano or a thiocyano group; Y is a hydrogen, bromo, chloro or iodo atom; and Z is a hydrogen atom.

5. The compound of claim 4, wherein $R^1$ is a methyl group $R^2$ is an ethyl group; X is a bromo atom; and Y is a hydrogen or bromo atom.

6. The compound of claim 1, wherein:

A is a chloro, bromo, fluoro, iodo, trifluoromethyl, trifluoromethoxy, methyl, ethyl, phenyl, methoxy chloromethyl, cyano or hydroxy group;

$A^1$ and B are each independently a hydrogen, chloro, bromo, fluoro or methyl group;

$R^1$ and $R^2$ are each independently a hydrogen atom or ($C_1$–$C_6$)alkyl group;

X is bromo, iodo, fluoro, ($C_1$–$C_2$)alkoxy or carbamoyloxy of the formula (—OC(O)N($R^3$)$_2$);

Y and Z are each independently a hydrogen, bromo, chloro, iodo, fluoro, cyano, thiocyano, isothiocyano, methylsulfonyloxy, thio($C_1$–$C_2$)alkyl, ($C_1$–$C_2$)alkoxy, carbamoyloxy of the formula (—OC(O)N($R^3$)$_2$), hydroxy, azide or ($C_1$–$C_4$)alkylcarbonyloxy group and either, but not both, Y or Z may be an imidazolyl or triazolyl group;

provided that when

X is ($C_1$–$C_2$)alkoxy or carbamoyloxy of the formula (—OC(O)N($R^3$)$_2$);

Y and Z are not a hydrogen, cyano thiocyano isothiocyano, methylsulfonyloxy, thio($C_1$–$C_2$)alkyl, ($C_1$–$C_2$)alkoxy, carbamoyloxy of the formula (—OC(O)N($R^3$)$_2$), azide, ($C_1$–$C_4$)alkylcarbonyloxy, imidazolyl, or triazolyl group;

and each $R^3$ is independently a hydrogen or a ($C_1$–$C_4$) alkyl group.

7. A method for controlling phytopathogenic fungi comprising applying to a plant, to plant seed for to a plant habitat a fungicidally-effective amount of the compound of claim 6.

8. A method for controlling phytopathogenic fungus comprising applying to a plant, to plant seed or to a plant habitat a fungicidally-effective amount of the compound of claim 1.

9. A method of claim 8 wherein the compound is applied in an amount from about 0.01 to about 20 kilograms per hectare.

10. The method of claim 8 wherein the fungus is from the Phycomycete or Basidiomycete class.

11. A method for controlling phytopathogenic fungi comprising applying to a plant, to plant seed or to a plant habitat a fungicidally-effective amount of the compound of claim 2.

12. The method of claim 11 wherein the fungi are selected from the class of Phycomycetes or Basidiomycete fungi and the compound is applied in an amount of from about 0.01 to about 20 kilograms per hectare.

13. A method for controlling phytopathogenic fungi comprising applying to a plant, to plant seed or to a plant habitat a fungicidally-effective amount of the compound of claim 4.

14. The method of claim 13 wherein the fungi are selected from the class of Phycomycetes or Basidiomycete fungi and the compound is applied in an amount of from about 0.1 to about 5 kilograms per hectare.

15. The method of claim 12 wherein the fungi cause late blight or downy mildew.

16. A fungicidal composition comprising the compound of claim 1 in a fungicidally-effective amount and an agronomically-acceptable carrier.

17. A fungicidal composition comprising the compound of claim 3 in a fungicidally-effective amount and an agronomically-acceptable carrier.

18. A fungicidal composition comprising the compound of claim 4 in a fungicidally-effective amount and an agronomically-acceptable carrier.

19. The compound N-[3'-(1',1'-dibromo-3'-methyl-2'-oxopentan)]-3,5-dichlorobenzamide.

* * * * *